(12) United States Patent
Lin et al.

(10) Patent No.: US 10,273,343 B2
(45) Date of Patent: Apr. 30, 2019

(54) CONDUCTIVE ELASTOMER, PREPARATION METHOD AND USE THEREOF

(71) Applicant: Soochow University, Suzhou (CN)

(72) Inventors: Xiao Lin, Suzhou (CN); Lei Yang, Suzhou (CN); Yanjie Bai, Suzhou (CN); Huilin Yang, Suzhou (CN)

(73) Assignee: SOOCHOW UNIVERSITY, Suzhou (CN)

( * ) Notice: Subject to any disclaimer, the term of this patent is extended or adjusted under 35 U.S.C. 154(b) by 62 days.

(21) Appl. No.: 15/541,699

(22) PCT Filed: Jul. 20, 2015

(86) PCT No.: PCT/CN2015/084531
§ 371 (c)(1),
(2) Date: Jul. 5, 2017

(87) PCT Pub. No.: WO2016/110082
PCT Pub. Date: Jul. 14, 2016

(65) Prior Publication Data
US 2018/0002509 A1    Jan. 4, 2018

(30) Foreign Application Priority Data
Jan. 6, 2015   (CN) .......................... 2015 1 0004341

(51) Int. Cl.
| | | |
|---|---|---|
| *C08K 3/16* | (2006.01) | |
| *C08K 3/28* | (2006.01) | |
| *C08L 3/04* | (2006.01) | |
| *A61L 24/00* | (2006.01) | |
| *A61L 24/02* | (2006.01) | |
| *A61L 24/08* | (2006.01) | |
| *C08L 3/02* | (2006.01) | |
| *C09J 9/02* | (2006.01) | |
| *C09J 11/04* | (2006.01) | |
| *C09J 103/02* | (2006.01) | |
| *H01B 1/22* | (2006.01) | |
| *H05K 1/09* | (2006.01) | |
| *C09D 11/52* | (2014.01) | |
| *C08B 30/14* | (2006.01) | |
| *H05K 1/03* | (2006.01) | |

(52) U.S. Cl.
CPC .............. *C08K 3/16* (2013.01); *A61L 24/001* (2013.01); *A61L 24/0042* (2013.01); *A61L 24/02* (2013.01); *A61L 24/08* (2013.01); *C08B 30/14* (2013.01); *C08K 3/28* (2013.01); *C08L 3/02* (2013.01); *C08L 3/04* (2013.01); *C09D 11/52* (2013.01); *C09J 9/02* (2013.01); *C09J 11/04* (2013.01); *C09J 103/02* (2013.01); *H01B 1/22* (2013.01); *H05K 1/092* (2013.01); *C08K 2003/162* (2013.01); *C08K 2003/164* (2013.01); *C08K 2003/166* (2013.01); *C08K 2003/168* (2013.01); *C08K 2003/287* (2013.01); *C08K 2201/001* (2013.01); *C08L 2203/02* (2013.01); *C08L 2203/20* (2013.01); *C08L 2205/025* (2013.01); *C08L 2205/03* (2013.01); *H05K 1/0393* (2013.01); *H05K 2201/0108* (2013.01); *H05K 2201/0314* (2013.01)

(58) Field of Classification Search
CPC ...... C08K 3/16; C08K 3/28; C08K 2003/287; C08K 2003/164; C08K 2003/166; C08K 2201/001; C08K 2003/162; C08K 2003/168; C08B 30/14; C09D 11/52; A61L 24/0042; A61L 24/001; A61L 24/08; A61L 24/02; C09J 103/02; C09J 9/02; C09J 11/04; H01B 1/22; H05K 1/092; H05K 2201/0108; H05K 2201/0314; H05K 1/0393; C08L 3/04; C08L 2203/20; C08L 2205/025; C08L 2203/02; C08L 2205/03; C08L 3/02
USPC .......................... 252/514.14, 519.32, 519.14
See application file for complete search history.

(56) References Cited

U.S. PATENT DOCUMENTS 9,212,273 B2 * 12/2015 Bosnyak .................. B60C 1/00
2006/0202171 A1    9/2006 Yoshida et al.
(Continued)

FOREIGN PATENT DOCUMENTS

CN    1129339 A    8/1996
CN    1786060 A    6/2006
(Continued)

OTHER PUBLICATIONS

Starch definition, Random House Kernerman Webster's College Dictionary, 2010. (Year: 2010).*

*Primary Examiner* — Douglas J McGinty
(74) *Attorney, Agent, or Firm* — SZDC Law P.C.

(57) ABSTRACT

A preparation method of a conductive elastomer includes the following steps: (1) according to the mass percent of 20~75%, dissolving the metallic salts into deionized water to form an electrolyte solution, wherein said metallic salts is either of magnesium nitrate, sodium nitrate, zinc nitrate, cesium nitrate, calcium nitrate, neodymium nitrate, aluminum nitrate, potassium nitrate, potassium chloride, magnesium chloride, calcium chloride, sodium chloride, zinc chloride, cesium chloride, aluminum chloride or their combinations; (2) according to the mass percent of 10~40%, mixing starches into the electrolyte solution prepared in step (1), then at the temperature of 33~120° C., stirring to gelatinize the starches, forming a viscous liquid; (3) standing the viscous liquid obtained in step (2) at 25~90° C. for 10 min to 48 h to obtain the conductive elastomer.

5 Claims, No Drawings

(56) References Cited

U.S. PATENT DOCUMENTS

2008/0242794 A1* 10/2008 Sandford ............... A01N 59/16
                                                     524/515
2011/0195264 A1*  8/2011 Aravinda ............. B22F 1/0007
                                                     428/546

FOREIGN PATENT DOCUMENTS

CN      102120265 A    7/2011
CN      104558699 A    4/2015

* cited by examiner

CONDUCTIVE ELASTOMER, PREPARATION METHOD AND USE THEREOF

This application is a national stage application of PCT/CN2015/084531, filed on Jul. 20, 2015, which claims priority to Chinese Patent Application No.: 201510004341.0, filed on Jan. 6, 2015, all of which are incorporated by reference for all purposes as if fully set forth herein.

FIELD OF THE INVENTION

The present invention relates to a kind of elastomer, its preparation method and use. More particularly, relates to a conductive elastomer and its preparation method and use. The present invention relates to the fields of flexible electronics, conductive adhesive and textile manufacturing, healthcare technology and so on.

TECHNICAL BACKGROUND

Starch, a kind of polysaccharide-based natural polymer, owns many advantages such as renewability, biodegradability, high stability, bio-safety and bio-compatibility. Thus, it has been widely applied in many technical fields such as healthcare technology. Starch granules get sticky after gelatinization in water and can dehydrate easily in the air. Most of starch-based adhesives rely on this property, such as what supplied in Chinese patents CN101054501A, CN102493274A, CN102757744A and CN 103897629 A.

Previous reports showed that stable starch elastomers that have excellent swelling property and water-retention capacity could be obtained by adjusting the molecular structure of starch or crosslinking with other macromolecules and polymers. For example, Chinese patent CN1480224A disclosed a hydrogel prepared with starch, polyvinylpyrrolidone, polyving akohol, water-soluble fibrin and water. The optimal weight percent of starch is within 5~15%. The mixture reveals a quasi-gel state initially, and finish the gelation by the exposure under electron beam or y ray with the absorbed dose at 5~50 kGy. Lamellar like gel adhesion could be induced when the absorbed dose is higher than 20 kGy, while cream like or semi liquid gel could be formed when the absorbed dose is low. The hydrogel has excellent swelling property and stickiness, with mechanical strength on the order of $10^{-2}$ MPa, the stretch ratio at fracture approximately 300%, and rate of water absorption between 1000%~8000%, which could be used as medical dressing and materials for delayed drug release. Chinese patent CN101982202A disclosed a kind of starch based hydrogel, which contains 10~30 wt. % starch and 2~15 wt. % water-soluble polymers. In addition, Salt condensation polymer and cross-linker were added during preparation with deionized water as the solvent. The hydrogel has high swelling degree, with the balanced swelling rate as approximately 300%. In addition, the hydrogel could keep wet, own high transparency, and proper mechanical strength. The Chinese patent CN 103833916 disclosed a method for preparing a starch acrylic acid based composite medical hydrogel. The hydrogel is prepared with gelatinized starch, 15~20% acrylic acid which is neutralized with alkaline, 12~16% N, N'-methylene bis acrylic amide, and 20~40% distilled water. The obtained hydrogel has high color stability, good water retention capability and bactericidal ability, and could be used efficiently for more than 720 h, which is suitable as a composite dressing. The above patents all prepared starch based hydrogel. However, all of them added polymers other than starch during preparation, and used cross-linker. The procedures are complicated and have great influence on the environment. The obtained hydrogels own limited ductility and almost have no conductive capability, which limit their applications in some fields.

The present conductive elastic materials are mainly electronic conductive which are prepared by mixing conductive particles or fibers. The Chinese patent CN 101918495 disclosed an electronic conductive elastomer, which is prepared by dispersing carbon nanotubes (CNTs) in the thermoplastic elastomer. The diameter of CNTs is 30~300 nm, and the aspect ratio is 10~100. The thermoplastic elastomer belongs to polyester system. CNTs were added with weight ratio of 0.01~10 to 100 elastomer. The bulk resistivity of the material is below $10^{11} \Omega \cdot cm$. The Chinese patent CN 102702662 A disclosed a kind of thermal and electrical conductive elastic material and the preparation method. The material is prepared by adding metal fibers, copper nanoparticles and expanded graphite into the styrene elastomer. And the mineral oil, polyolefin, and antioxidant are added as extra additives. The prepared materials are heat conductive, electronic conductive (volume electronic resistance is approximately $10^3 \Omega \cdot cm$, soft with low hardness.

In addition to adding conductive elementary substances, the metallic salts could also be added to prepare polymeric electrolytes, which are ionic elastomers, through the complexation of alkali metal ions with the polyether block. The Chinese patent CN 103131165 A disclosed a conductive PA12 elastomer and the preparation method. The elastomer was prepared by adding alkali metallic salts into the PA12 elastomer, with addition materials including antioxidant, heat stabilizer, and conductive agent. The cations in the alkali metallic salts could be $Li^+$, $Na^+$ and $K^+$, and the anions could be $Cl^-$, $Br^-$, $I^-$, and $ClO_4^-$. This elastomer own advantages including stable and high conductivity (surface resistance of $10^2 \sim 10^3 \Omega \cdot cm$), low cost, good heat resistance. However, this conductive elastomer use thermal plastic elastomer as the substrate, which has limited stretchability, limited its applications.

DETAILED DESCRIPTION OF THE INVENTION

The objective of this invention is to supply a kind of biodegradable, self-adhesive, highly transparent, environmentally friendly, and bio-safe conductive elastomer, preparation method and use thereof, in order to overcome the disadvantage of present conductive elastomer.

The technical solution to realize the objective is, a preparation method of a conductive elastomer, comprising the following steps:

(1) according to the mass percent of 20~75%, dissolving the metallic salts into deionized water to form an electrolyte solution, wherein said metallic salts is either of magnesium nitrate, sodium nitrate, zinc nitrate, cesium nitrate, calcium nitrate, neodymium nitrate, aluminum nitrate, potassium nitrate, potassium chloride, magnesium chloride, calcium chloride, sodium chloride, zinc chloride, cesium chloride, aluminum chloride or their combinations;

(2) according to the mass percent of 10~40%, mixing starches into the electrolyte solution prepared in step (1), then at the temperature of 33~120° C., stirring to gelatinize the starches, forming a viscous liquid;

(3) standing the viscous liquid obtained in step (2) at 25~90° C. for 10 min 4 to 48 h to obtain the conductive elastomer.

In the present invention, said starches is either original or modified corn, potato, wheat and barley, cassava, sweet potato, sticky rice starches or their combinations.

The present invention also include a conductive elastomer prepared according to the above mentioned method, the resistivity of said conductive elastomer is $1\sim1\times10^4 \Omega\cdot cm$; stretch ratio at elastic region is 1000~2500%, stretch ratio at fracture is 1500%~9000%; said conductive elastomer has bio-degradability and autofluorescence with emitting wavelength at 400~500 nm.

In the present invention, the conductive elastomer is water soluble when said metallic salts is either of zinc nitrate, cesium nitrate, calcium nitrate, neodymium nitrate, aluminum nitrate, potassium nitrate, potassium chloride, calcium chloride, zinc chloride, cesium chloride, aluminum chloride or their combinations.

The present invention supplies the use of a conductive elastomer, which includes using in preparations of flexible circuits, conductive adhesive, conductive textile, medical and wound dressing, biomedical sealant or drug release system.

The conductive elastomer bases on an elastic matrix that is a specific gelatinized starch. The electrolyte with high concentration of metallic salts is used as the conductive agent. The conductive elastomer is prepared by getting the specific electrolyte involved in the gelatinization process of specific starch. The stretch ratios at elastic region and fracture, and resistivity of the conductive elastomer are between 1000~2500%, 1500%~9000%, $1\sim1\times10^4 \Omega\cdot cm$, respectively. It also has autofluorescence.

Compared with the prior art, the present invention solves the problem that gelatinized starches tend to loss water and become dry and brittle by supplying a stable conductive elastomer through making the specific electrolyte involved in the gelatinization process of specific starch. The conductive elastomer could be used in the preparations of flexible circuits, conductive adhesive, conductive textile, wound dressing, as well as tissue adhesion, drug release.

More importantly, this conductive elastomer has several advantages compared with the present conductive soft materials. Firstly, it is biodegradable, thus could be used for the design of biodegradable circuits, the fabrication of biodegradable conductive adhesive and conductive textiles. Secondly, it owns excellent stretchability and good stickiness, which could be used for the preparation of electric devices with high stretchability, and biomedical sealant. Thirdly, it has autofluorescence, which is helpful for the detection and monitoring the elastomer in devices or in vivo.

In summary, this invention has the following benefits compared with the existing materials and preparation methods:

1. The raw materials for preparing the elastomer have abundant sources, are cost effective, environmentally friendly, and safe to human.

2. The preparation method is simple with low requirement for equipment, easy to realize large scale production and environmentally friendly.

3. This conductive elastomer simultaneously owns high elasticity, high conductivity, biodegradability, autofluorescence, good stickiness, high transparency, and is environmentally friendly and nontoxic, which could be used in the preparations of flexible circuits, conductive adhesives, conductive textile, medical and wound dressing, biomedical sealant or drug release system.

PREFERRED EMBODIMENTS

Embodiment 1

An electrolyte solution was prepared by dissolving 3.5 g of magnesium chloride in 9 ml of deionized water at room temperature or by heating. Then 4 g of corn starch was added in the electrolyte and gelatinized at 60° C., continuously stirring to obtain a viscous liquid. Then let the viscous liquid standing at 25° C. for 40 h, forming a semi-transparent conductive elastomer.

The mechanical properties of the elastomer were measured by uniaxial tensile test. The results showed that the stretch ratios at elastic region and fracture were 1100% and 1700%, respectively. The conductivity of the elastomer was measured by constant voltage test. The results showed that the volume resistivity was $5.7\times10^3 \Omega\cdot cm$. It also had autofluorescence with an emitting wavelength at 450 nm. The adhesive strength of elastomer measured by tensile detachment test on polished pure copper was 50 kPa.

The elastomer was used for the preparation of flexible circuits: The viscous liquid after gelatinization of starch was filled in a printer, and printed into circuits on a flexible substrate. The flexible circuits were formed after aging for 24 h.

The elastomer was used for the preparation of conductive textile: The viscous liquid after gelatinization of starch was placed in a vacuum chamber under a vacuum <10 kPa for 15 min. The viscous liquid was coated on textile and aged at 40° C. for 12 h, forming conductive textile whose surface resistivity is $2.4\times10^4 \Omega/\square$.

The elastomer could be totally dissolved in water whose volume was 15 times of that of the elastomer.

Embodiment 2

The metallic salts in Table 1 were dissolved in 10 ml of deionized water using the weight percentages shown in Table 1. Then 3 g of sweet potato starch was added in the solutions and gelatinized at 50° C., continuously stirring to form viscous liquids. Then the liquids were aged at 37° C. for 4 h to obtain the semi-transparent conductive elastomers. The volume resistivity, stretch ratios at elastic region and fracture of the elastomers were measured using methods in Embodiment 1. The results were listed in Table 1.

TABLE 1

Volume resistivity, stretch ratios at elastic region and fracture of the elastomers prepared with different metallic salts.

| No. | Metallic salts | Weight percent (%) | Volume resistivity ($\Omega \cdot cm$) | Stretch ratio at elastic region (%) | Stretch ratio at fracture (%) |
|---|---|---|---|---|---|
| 1 | Zinc nitrate | 50 | 110.1 | 1366.4 | 2912.3 |
| 2 | Magnesium nitrate | 20 | 7891.1 | 1155.6 | 1510.6 |
| 3 | Sodium nitrate | 30 | 692.3 | 2356.7 | 3521.6 |
| 4 | Cerium nitrate | 25 | 45.2 | 1399.2 | 2614.2 |
| 5 | Calcium nitrate | 35 | 556.7 | 1268.2 | 2900.5 |
| 6 | Neodymium nitrate | 60 | 289.1 | 1366.2 | 6789.2 |
| 7 | Aluminum nitrate | 75 | 3.6 | 2157.9 | 3687.5 |
| 8 | Potassium chloride | 40 | 74.5 | 1124.1 | 2510.2 |
| 9 | Calcium chloride | 50 | 965.1 | 1241.2 | 8769.5 |
| 10 | Sodium chloride | 45 | 138.9 | 1921.9 | 1899.2 |
| 11 | Zinc chloride | 55 | 2166.5 | 1221.3 | 1906.5 |
| 12 | Cerium chloride | 65 | 97.2 | 1354.5 | 7566.7 |
| 13 | Aluminum chloride | 70 | 5.4 | 1287.2 | 2817.6 |
| 14 | Potassium chloride | 5 | 2.2 | 1355.4 | 2546.2 |

TABLE 1-continued

Volume resistivity, stretch ratios at elastic region and fracture of the elastomers prepared with different metallic salts.

| No. | Metallic salts | Weight percent (%) | Volume resistivity ($\Omega \cdot cm$) | Stretch ratio at elastic region (%) | Stretch ratio at fracture (%) |
|---|---|---|---|---|---|
| 15 | Aluminum nitrate | 10 | 6690.7 | 1156.2 | 4987.6 |
|  | Sodium nitrate | 5 |  |  |  |
|  | Calcium chloride | 20 |  |  |  |
|  | Neodymium nitrate | 30 |  |  |  |
|  | Zinc nitrate | 20 |  |  |  |

Embodiment 3

4 g of zinc chloride was dissolved in 8 ml of deionized water. Then the starches listed in Table 2 were added to the solutions using the weight percentages shown in Table 2, stirring under the temperature in Table 2 to obtain a viscous liquid, then let the viscous liquid standing at 60° C. for 4 h, to obtain semi-transparent conductive elastomers. The volume resistivity, stretch ratios at elastic region and fracture of the elastomers were measured and the results were listed in Table 2.

TABLE 2

Volume resistivity, stretch ratios at elastic region and fracture of the elastomers prepared with different starches.

| Test No. | Starches | Weight percent (%) | Temperature (° C.) | Volume resistivity ($\Omega \cdot cm$) | Stretch ratio at elastic region (%) | Stretch ratio at fracture (%) |
|---|---|---|---|---|---|---|
| 1 | Corn | 10 | 65 | 1230.5 | 1455.6 | 2187.3 |
| 2 | Potato | 25 | 55 | 2236.6 | 1103.6 | 2513.6 |
| 3 | Wheat | 35 | 65 | 2514.5 | 1261.5 | 3514.2 |
| 4 | Barley | 20 | 60 | 2615.3 | 1355.6 | 2354.2 |
| 5 | Sweet potato | 15 | 80 | 3621.5 | 1261.2 | 2155.2 |
| 6 | Sweet potato | 30 | 70 | 2531.2 | 1356.2 | 3654.3 |
| 7 | Cassava | 40 | 60 | 1987.6 | 1245.3 | 3123.2 |
| 8 | Glutinous rice | 25 | 60 | 1875.2 | 1231.6 | 2917.2 |
| 9 | Modified corn | 30 | 65 | 2621.3 | 1566.3 | 2899.1 |
| 10 | Potato | 10 |  |  |  |  |
|  | Red sweet potato | 10 | 55 | 2465.7 | 1366.2 | 3412.8 |
|  | White sweet potato | 15 |  |  |  |  |

Embodiment 4

Opaque conductive elastomer was obtained by vigorously stirring the viscous liquid after gelatinization of starch in Embodiment 1 and aged at 50° C. for 2 hours. And the transparent conductive elastomer was obtained by placing the viscous liquid after gelatinization of starch in Embodiment 1 in vacuum chamber under a vacuum <10 kPa for 15 min and aged at 50° C. for 20 hours.

The transparent conductive elastomer provided in this example was used for the tissue adhesion of the myocardial defect: the rat model of myocardial defect was made, and then the elastomer (after exposure to UV irradiation to sterilization) was applied to the defect, and it was observed that the elastomer could be tightly attached to the surface of the heart and adhered the defect parts together.

What we claim:

1. A preparation method of a conductive elastomer, consisting of:
    (1) according to the mass percent of 20~75%, dissolving metallic salts into deionized water to form an electrolyte solution, wherein said metallic salts is magnesium nitrate, sodium nitrate, zinc nitrate, cesium nitrate, calcium nitrate, neodymium nitrate, aluminum nitrate, potassium nitrate, potassium chloride, magnesium chloride, calcium chloride, sodium chloride, zinc chloride, cesium chloride, aluminum chloride or a combination thereof;
    (2) according to the mass percent of 10~40%, mixing starches into the electrolyte solution prepared in step (1), then at the temperature of 33~120° C., stirring to gelatinize the starches, forming a viscous liquid;
    (3) standing the viscous liquid obtained in step (2) at 25~90° C. for 10 min to 48 h to obtain the conductive elastomer.

2. The preparation method of a conductive elastomer according to claim 1, wherein said metallic salts is zinc nitrate, cesium nitrate, calcium nitrate, neodymium nitrate, aluminum nitrate, potassium nitrate, potassium chloride, calcium chloride, zinc chloride, cesium chloride, aluminum chloride a combination thereof.

3. The preparation method of a conductive elastomer according to claim 1, wherein said starches is original or modified corn, potato, wheat and barley, cassava, sweet potato, sticky rice starches or a combination thereof.

4. A conductive elastomer prepared according to the method in claim 1, wherein the resistivity of said conductive elastomer is $1\sim1\times10^4 \Omega \cdot cm$; stretch ratio at elastic region is 1000~2500%, stretch ratio at fracture is 1500%~9000%; said conductive elastomer has bio-degradability and autofluorescence with emitting wavelength at 400~500 nm.

5. A conductive elastomer prepared according to the method in claim 2, wherein said conductive elastomer is water soluble.

* * * * *